United States Patent
Grek et al.

(10) Patent No.: US 9,861,290 B1
(45) Date of Patent: Jan. 9, 2018

(54) WIRELESS MEDICAL SENSOR SYSTEM

(71) Applicant: Rittenhouse Engineering, LLC, St. Johns, FL (US)

(72) Inventors: Mark Grek, Gainesville, FL (US); Sasha B. Grek, Gaineville, FL (US)

(73) Assignee: Rittenhouse Engineering, LLC, Jacksonville, FL (US)

( * ) Notice: Subject to any disclaimer, the term of this patent is extended or adjusted under 35 U.S.C. 154(b) by 0 days.

(21) Appl. No.: 14/297,586

(22) Filed: Jun. 5, 2014

Related U.S. Application Data

(60) Provisional application No. 61/831,461, filed on Jun. 5, 2013.

(51) Int. Cl.
| | | |
|---|---|---|
| *A61B 5/04* | (2006.01) | |
| *A61B 5/0408* | (2006.01) | |
| *A61B 5/0402* | (2006.01) | |
| *A61B 5/0428* | (2006.01) | |

(52) U.S. Cl.
CPC ........ *A61B 5/04085* (2013.01); *A61B 5/0402* (2013.01); *A61B 5/0408* (2013.01); *A61B 5/0428* (2013.01)

(58) Field of Classification Search
CPC . A61B 5/0006; A61B 5/04082; A61B 5/0402; A61B 5/0408; A61B 5/0428
USPC ........................................ 600/513, 387, 390
See application file for complete search history.

(56) References Cited

U.S. PATENT DOCUMENTS

| | | | |
|---|---|---|---|
| 4,681,118 A | * | 7/1987 | Asai .................... A61B 5/0006 128/903 |
| 5,511,553 A | | 4/1996 | Segalowitz |
| 5,579,001 A | | 11/1996 | Dempsey et al. |
| 5,687,734 A | | 11/1997 | Dempsey et al. |
| 5,862,803 A | | 1/1999 | Besson et al. |
| 5,936,539 A | | 8/1999 | Fuchs |
| 6,238,338 B1 | | 5/2001 | DeLuca et al. |
| 6,416,471 B1 | | 7/2002 | Kumar et al. |
| 6,441,747 B1 | | 8/2002 | Khair et al. |
| 6,494,829 B1 | | 12/2002 | New, Jr. et al. |
| 6,847,913 B2 | | 1/2005 | Wigley et al. |
| 7,187,961 B2 | | 3/2007 | Yamashita et al. |
| 7,206,630 B1 | | 4/2007 | Tarler |
| 7,248,894 B2 | | 7/2007 | Fujieda et al. |
| 7,316,648 B2 | | 1/2008 | Kelly et al. |
| 7,387,607 B2 | | 6/2008 | Holt et al. |

(Continued)

*Primary Examiner* — Carl H Layno
*Assistant Examiner* — Jon Eric C Morales
(74) *Attorney, Agent, or Firm* — Wolf, Greenfield & Sacks, P.C.

(57) ABSTRACT

A wireless biometric lead set in which one or more biometric sensors are hermetically sealed in a package. The lead set may contain multiple such sensors and packages, with other components to operate the lead set, such as a power source, a transmitter, and a charging device. Such a lead set may be sterilized for reuse and may be configured to easily fit into existing medical facility work flows. The lead set may automatically, associate with a specific monitoring device. That monitoring device may selectively process data transmitted from the associated lead set. Further, low power operation may be achieve via multiple operating modes, such as modes in which no actions are performed, samples are taken and accumulated, or accumulated samples are transmitted. An interface device may allow the lead set to be used with a conventional monitoring device.

21 Claims, 11 Drawing Sheets

(56) References Cited

U.S. PATENT DOCUMENTS

| | | |
|---|---|---|
| 7,583,190 B2 | 9/2009 | Reggiardo et al. |
| 7,620,438 B2 | 11/2009 | He |
| 7,676,380 B2 | 3/2010 | Graves et al. |
| 7,782,192 B2 | 8/2010 | Jeckelmann et al. |
| 8,073,008 B2 | 12/2011 | Mehta et al. |
| 8,085,151 B2 | 12/2011 | Jennewine |
| 8,155,982 B2 | 4/2012 | Dicks et al. |
| 8,172,752 B2 | 5/2012 | Russ |
| RE43,767 E | 10/2012 | Eggers et al. |
| 2002/0180605 A1 | 12/2002 | Ozguz et al. |
| 2004/0073127 A1* | 4/2004 | Istvan et al. ............... 600/513 |
| 2005/0119533 A1 | 6/2005 | Sparks et al. |
| 2005/0131288 A1 | 6/2005 | Turner et al. |
| 2006/0085041 A1* | 4/2006 | Hastings et al. ............ 607/33 |
| 2008/0004904 A1 | 1/2008 | Tran |
| 2008/0281168 A1 | 11/2008 | Gibson et al. |
| 2010/0056886 A1 | 3/2010 | Hurtubise et al. |
| 2012/0001751 A1 | 1/2012 | Baker et al. |
| 2012/0197150 A1* | 8/2012 | Cao ................. A61B 5/6823 600/523 |
| 2012/0209102 A1* | 8/2012 | Ylotalo et al. ............. 600/397 |

\* cited by examiner

WIRELESS MEDICAL SENSOR SYSTEM

CROSS-REFERENCE TO RELATED APPLICATIONS

This application claims the benefit under 35 U.S.C. §119(e) of U.S. Provisional Application Ser. No. 61/831,461, entitled "WIRELESS MEDICAL SENSOR SYSTEM" and filed on Jun. 5, 2013, and which is hereby incorporated herein by reference in its entirety.

BACKGROUND

Traditional intensive care unit (ICU) and emergent care electrocardiograph (ECG) monitoring equipment is typically composed of a passive contact or non-contact patient interface lead frame, a passive hookup cable, and an active bedside monitor or similar piece of equipment that also performs the function of passing telemetry information acquired from the passive lead set into the monitoring infrastructure. In this case, the only active electronics in the system are contained within the bedside monitor function. Noteworthy is that the disposable or reusable patient leads and hookup cable are not responsible for actively monitoring, recording, or propagating the ECG information to displays, monitoring stations or other information technology (IT) infrastructure of the containing facility.

FIG. 1 is a schematic illustration of a wired ECG monitoring system. Electrical signal information from patient 102 is obtained at passive contacts 103a-c connected to the patient's body. Electrical signals are transmitted via patient leads 104a-c to hook-up cable assembly 106 and bed-side monitor 108, which limit the available space surrounding the patient's bed. Active electronics for performing measurement are found in bed-side monitor 108. Bed-side display 110 shows the measurement information obtained by bed-side monitor 108 for the use of clinicians who are in physical proximity to the patient. Measurement information may be sent from bed-side monitor 108 to an IT infrastructure 112, which may then send the information to a remote monitoring station, such as a nurse's station, or a patient telemetry database.

A similar technique is deployed by current existing wireless systems in the market, which simply deploy a more portable version of the bed-side monitor, where the bedside monitor is usually reduced in form-factor and worn as an accessory to the patient, either carried or affixed via adjustable strap or band:

FIG. 2 is a schematic illustration of a wireless ECG monitoring system. Electrical signal information from patient 102 is obtained at passive contacts 103a-c connected to the patient's body. The obtained electrical signals are transmitted via patient leads 104a-c to portable equipment 202, which contains electronics and equipment configured to enable wireless transmission of information to a bed-side display. Portable equipment 202 may contain substantially all the electronics previously found in hook-up cable assembly 106 and/or bed-side monitor 108. Wireless transceiver device 202 is physically affixed to the patient's arm using a simple arm band 204.

In the case of FIG. 2, the ECG monitor can be wirelessly connected via Wi-Fi packet-based data protocols or other wireless/radio-frequency (RF) technologies such as low-power Bluetooth to IT infrastructure and subsequent remote monitoring stations to propagate the patient data. The portable equipment 202 also makes use of passive disposable or reusable leads that connect the patient to the active electronics residing with the portable unit.

This overall passive lead/base station model is also used with oxygen saturation ($SpO_2$)/pulse-ox (oximetry) vital monitoring systems that are typically used in a standard emergency room (ER)/ICU patient monitoring configuration.

These sensing techniques are relatively easy and cost-effective for health care institutions to implement.

SUMMARY

Disclosed herein are systems and methods for wireless patient monitoring. Inventive concepts as described herein may be embodied in any of one or more forms, including a method of patient monitoring, wireless lead sets adapted to be attached to a patient to collect medical data, a method of operation of wireless lead sets adapted to be attached to a patient to collect medical data, a method of operating a monitoring device that receives data from wireless lead sets, a non-transitory computer-readable storage medium encoded with computer-executable instructions to control operation of a monitoring device, an interface device that adapts a monitoring device designed for wired leads to operate with wireless leads, and/or a system involving wireless leads and one or more monitoring devices. A system as described herein may be implemented using techniques as are known in the art.

Accordingly, in accordance with one aspect of the invention, a wireless biometric lead set is disclosed, which may comprise a plurality of hermetically sealed packages, each of the plurality of hermetically sealed packages containing a biometric sensor, and each of the plurality of hermetically sealed packages being configured to be attached to a body. The a wireless biometric lead set also comprises conductors interconnecting the plurality of hermetically sealed packages; a power source; and a transceiver.

The wireless biometric lead set may further comprise a plurality of semiconductor devices comprising circuitry for conditioning a signal from a biometric sensor, wherein the plurality of semiconductor devices may be contained within a hermetically sealed package of the plurality of hermetically sealed packages. The power source may comprise a battery and/or an energy harvesting and storage module. The plurality of hermetically sealed packages may comprise a first hermetically sealed package, a second hermetically sealed package, and a third hermetically sealed package; and the power source may be disposed within the first hermetically sealed package, and the transceiver may be disposed within the second hermetically sealed package.

The wireless biometric lead set may further comprise a wireless recharging coil disposed within the third hermetically sealed package. The biometric sensor contained within each of the plurality of hermetically sealed packages may be an electrocardiograph (ECG) sensor. The wireless biometric lead set may further comprise a controller; and a memory, wherein the controller may be configured to: accumulate in the memory samples from a biometric sensor in a hermetically sealed package of the plurality of hermetically sealed packages, the samples being accumulated at first intervals; and transmit, at second intervals longer than the first intervals, the samples accumulated in the memory.

In accordance with another aspect of the invention, a method of operating a wireless biometric lead set for monitoring a patient is disclosed, which method may comprise: receiving, via wireless communication, a key associated with the wireless biometric lead set; associating the key with a monitoring station; transmitting measured biometric data from the wireless biometric lead set in connection with the key; at the monitoring station, selecting data for patient monitoring based on the associated key.

Receiving the key associated with the wireless biometric lead set may comprise, in response to detecting that the wireless biometric lead set is out of communication with the monitoring station, searching for a transmission comprising the key. The wireless biometric lead set may be connected to the monitoring device for charging and disconnected from the monitoring device for use in monitoring a patient. Receiving the key associated with the wireless biometric lead set may comprise with a proxy device in proximity to the wireless biometric lead set, receiving the key; moving the proxy device in proximity to the monitoring device; and with the proxy device in proximity to the monitoring device, transferring the key to the monitoring device.

The method may further comprise accumulating measured biometric data samples within the wireless biometric lead set; transmitting, at intervals, the accumulated measured biometric data samples. The wireless biometric lead set may operate in a first power consumption mode when the accumulated measured biometric data samples are transmitted and at a second power consumption mode during intervals in which the accumulated measured biometric data samples are not transmitted, more power being consumed in the first power consumption mode than in the second power consumption mode. The intervals may be first intervals; the measured biometric data samples may be collected at second intervals, shorter than the first intervals; and the second power consumption mode may comprise a first submode during which the measured biometric data samples are being acquired and a second submode during which the measured biometric data samples are not being acquired.

The measured biometric data samples may comprise samples from a plurality of ECG sensors. Selecting data for patient monitoring may comprise monitoring a first patient; and the method may further comprise sterilizing the wireless biometric lead set and reusing the wireless biometric lead set for monitoring a second patient.

In accordance with another aspect of the invention, an interface device adapted to configure a monitoring device for operation with a wireless biometric lead set is disclosed. The interface device may comprise: a charging station for the wireless biometric lead set; a connector configured to connect to a monitoring device; a wireless receiver; and a controller, adapted to perform a radio frequency (RF) association with the wireless biometric lead set and to transfer data received from the associated wireless biometric lead set from the receiver through the connector. The controller may be configured to respond to an indication that the wireless biometric lead set is disconnected from the charging station by performing an RF association routine. The interface device may further comprise a holder for holding the wireless biometric lead set at the charging station. The interface device may further comprise a dongle configured for insertion into a lead port of the monitoring device.

The foregoing is a non-limiting summary of the invention, which is defined by the attached claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

The inventors have recognized and appreciated that significant advantages may be provided in a health care setting with a bio sensor lead set having hermetically sealed packages containing sensor elements, such as ECG electrodes. The lead set may support one or more low power modes of operation, even though it wirelessly communicates data to a monitoring device. As a result, a patient being monitored with the lead set may move or be moved around the health care facility. Though, in some embodiments communication directly to a wide area network may be possible.

The lead set may be sterilized and reused. And, though components are sealed within hermetic packages, operation may be relatively simple. For example, the lead set may easily, and in some scenarios automatically, associate with a specific monitoring device, such that, regardless of where the patient is located measured data may be received and processed and associated with a specific patient.

Figure 1:
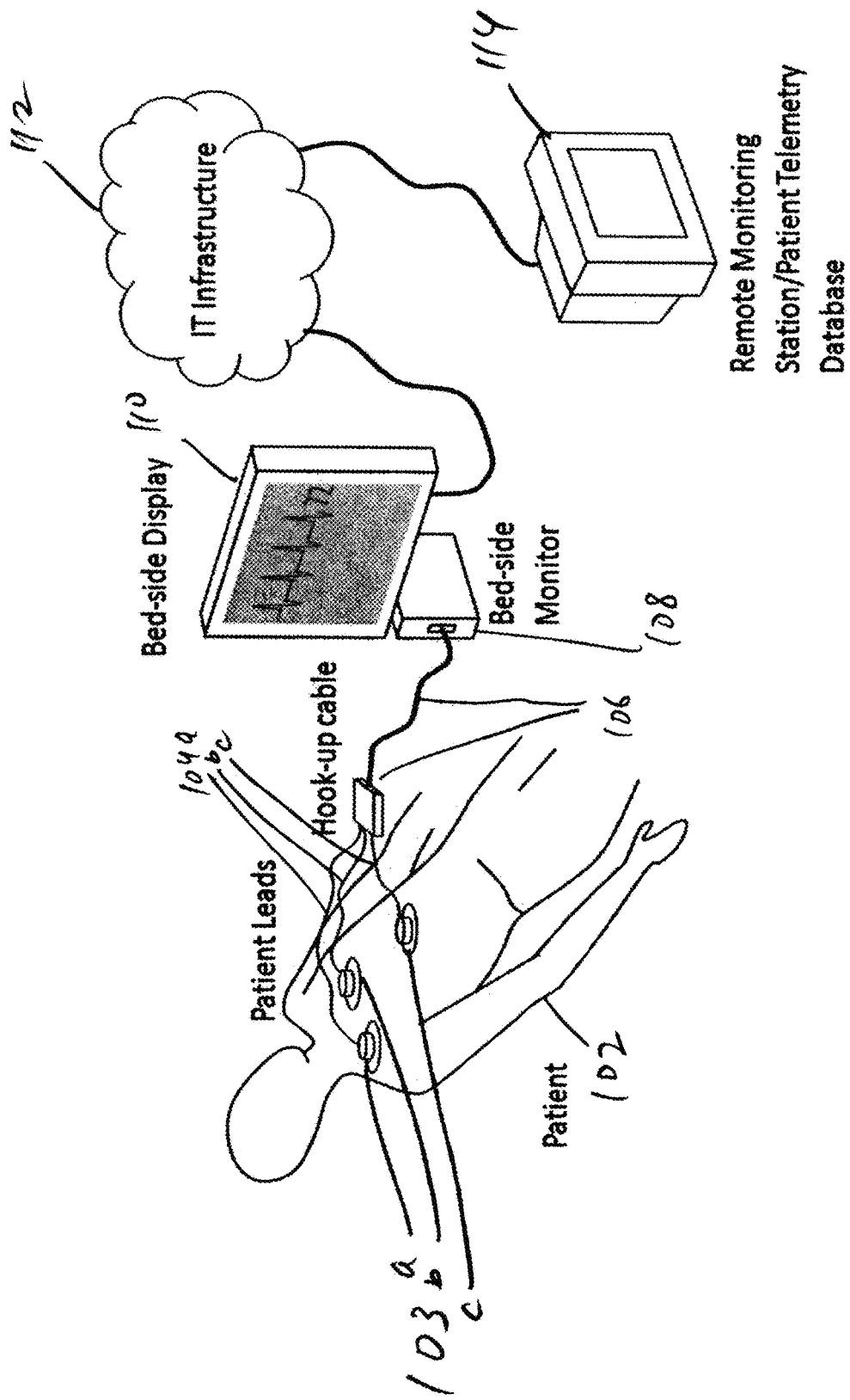
FIG. 1 is a schematic illustration of a wired ECG monitoring system.
Figure 2:
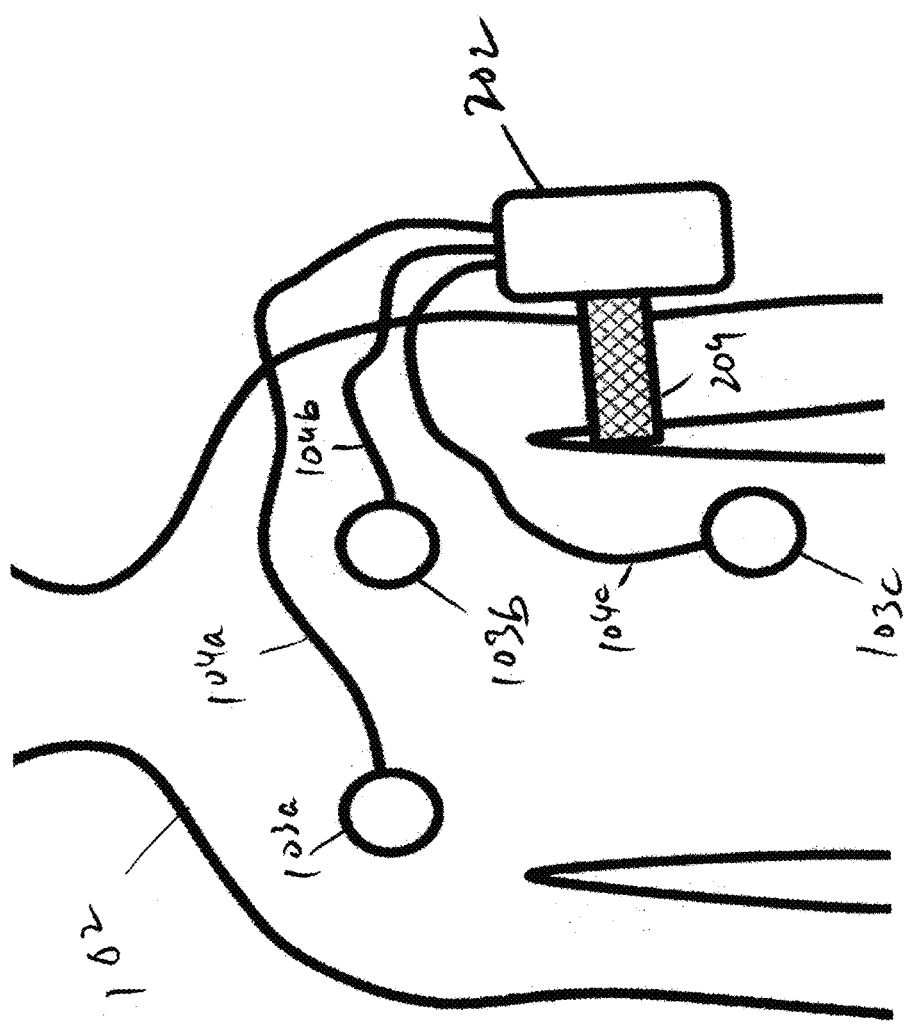
FIG. 2 is a schematic illustration of a wireless ECG monitoring system.

Moreover, the lead set may be simply assembled at low cost using techniques as are known in the art. Such components may be configured and controlled to provide additional functionality as described herein. FIG. 2 illustrates a known system, and is illustrative of the types of components that might be integrated into a lead set as described herein.

In the case of FIG. 2, the ECG monitor can be wirelessly connected via Wi-Fi data packet or other wireless/radio-frequency (RF) technologies such as low-power Bluetooth to IT infrastructure and subsequent remote monitoring stations to propagate the patient data. The portable equipment also makes use of passive disposable or reusable leads that connect the patient to the active electronics residing with the portable unit. Note that this overall passive lead/base station model is also used with oxygen saturation ($SpO_2$)/pulse-ox (oximetry) vital monitoring systems that are comprise a standard ER/ICU patient monitoring configuration.

These sensing techniques are relatively easy and cost effective for health care institutions to implement; however, the implementations above fall short of utilizing the capabilities of wireless sensor integration as deployed in other industries.

An ECG is obtained with the following basic elements as in traditional methods: the leads/pads themselves, the hookup cable, and the bedside monitor which can be broken down into more granular components. Specifically, these components include amplification, analog buffering and/or filtering components, which may perform signal conditioning. Signals may be converted to an analog-to-digital converter (ADC) with a processor, controller, or similar-functioning ASIC or device for further processing. For example, the digitized information may be used for a bedside display output or transmitted to other monitoring points such as the remote monitoring station.

Figure 3:
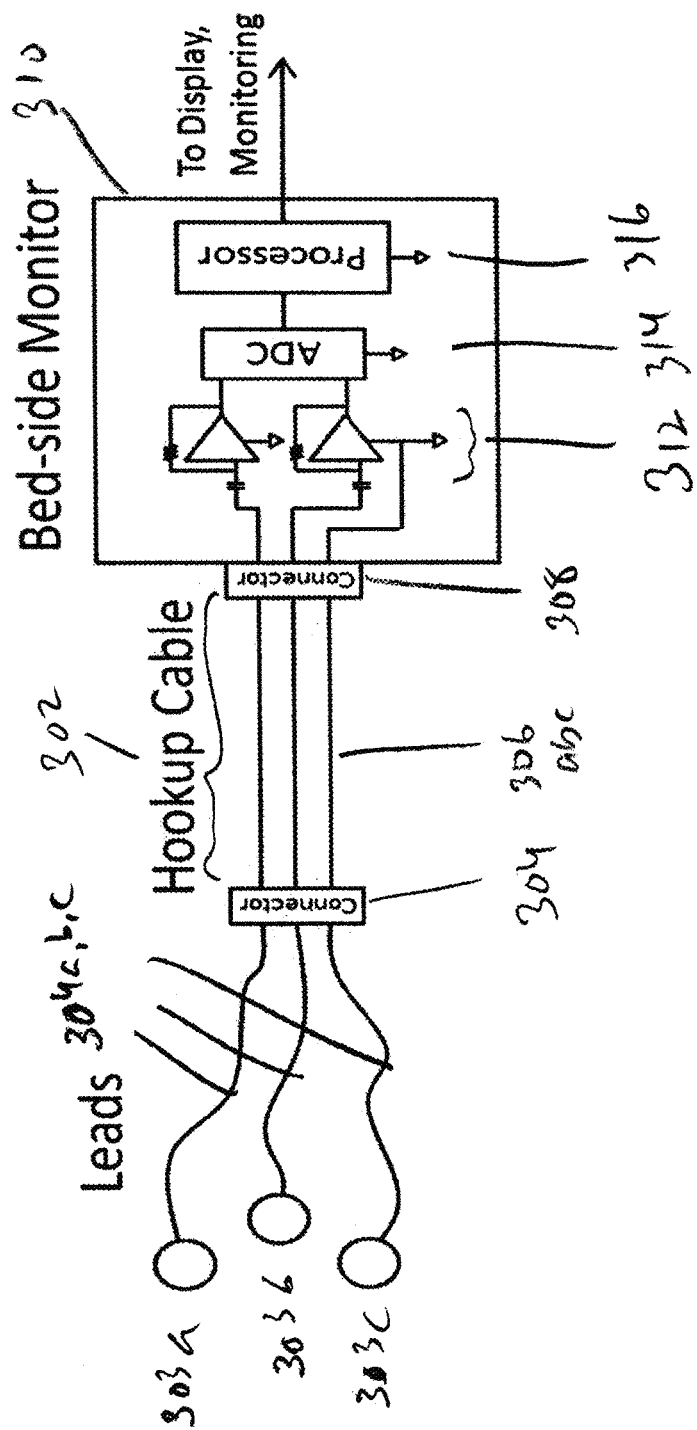
FIG. 3 is a schematic illustration of available components in a wired ECG monitoring system.

FIG. 3 is a schematic illustration of representative available components in a wired ECG monitoring system. Electrical signal information from the patient is obtained at contacts 303a-c connected to the patient's body. The obtained electrical signals are transmitted via patient leads 304a-c to a hookup cable 302, which comprises a connector 304 for physically coupling the patient leads to the hookup cable, conductors 306a-c for individually transmitting the electrical signals on each patient lead via a separate conductor, and connector 308 for physically coupling the hookup cable with a bed-side monitor 310. The hookup cable thus enables transfer of electrical signals from patient leads 304a-c to bed-side monitor 310.

Bed-side monitor 310 includes analog amplifiers 312, analog-to-digital converter (ADC) 314, and processor 316, which together process the received electrical signal information to produce data relating to the patient in a selected format. Specifically, ADC 314 is responsible for converting analog electrical signals into digital signals, which are then processed by processor 316. This data, which may be referred to as patient telemetry, may be sent to the bed-side monitor's display screen, or to a monitoring station.

However, the use of wireless technology offers many advantages in the clinical environment. One significant advantage is the improvement of work flow made possible by the absence of a physical connection between the leads and the bed-side monitor. Whereas previously a clinician would have not been able to access the area directly in front of the patient occupied by the physical lead wires, the use of wireless leads allows the clinician to walk around the patient without interfering with the operation of the monitor. Patient access, maintenance (patient turning), patient mobility, patient relocation, and bed positioning without being constrained by monitoring equipment are all improved.

Alternatively, in some embodiments, Wi-Fi and other RF-based portable monitors will use any combination of leads and hookup cables with a battery as well as an RF subsystem, e.g. a modem, RF System-on-Chip (SoC) or similar application-specific integrated circuit (ASIC), to broadcast the patient telemetry to a corresponding receiver. Note that signal flow may be the same, including lead type, connection, and participation in the patient electrical signal chain prior to digitization, as described below in relation to FIG. 4.

Figure 4:
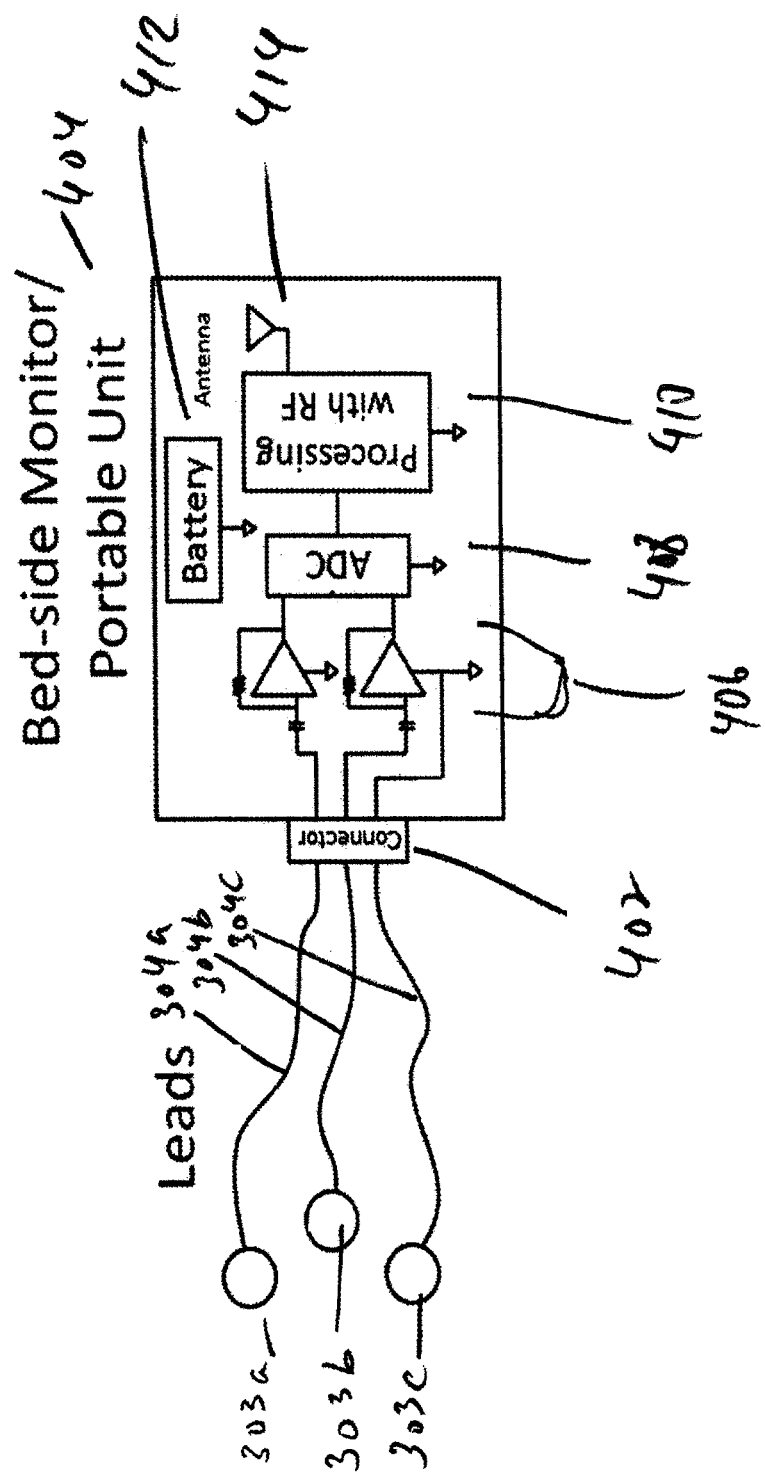
FIG. 4 is a schematic illustration of available components in a wireless ECG monitoring system.

FIG. 4 is a schematic illustration of representative available components in a wireless ECG monitoring system. As described previously in connection with FIG. 3, electrical signal information from the patient is obtained at contacts 303a-c connected to the patient's body. The obtained electrical signals are transmitted via patient leads 304a-c to connector 402. Connector 402 physically interfaces each individual lead 304a-c to bed-side monitor/portable unit 404. Bed-side monitor/portable unit 404, which may be worn on a patient's arm or otherwise affixed to the patient or to the surrounding environment of a patient, includes analog amplifiers 406, ADC 408, and processor 410. Additionally, bed-side monitor/portable unit 404 includes battery 412, for providing power to the bed-side monitor/portable unit 404 when not physically connected to electrical power, and antenna 414 to transmit and receive radio frequency (RF) signals. Processor 410 may also be augmented to include wireless processing functions for generating and decoding RF signals. In some embodiments, processor 410 may comprise two physically separate components for performing non-RF and RF processing, respectively.

The RF signal from the bedside monitor/portable unit may be handled in at least two ways, which in either case encapsulates the ECG data into standard data packets. In the case of Wi-Fi, the packet may be directly decoded from a digital format by a receiving bed-side or station monitor or otherwise acquisition hardware. In the case of low-power Bluetooth and proprietary RF solutions, the data can be converted by a specialized receiving unit that in turn creates a digital medical infrastructure packet according to the specific network protocol (e.g., LAN, Wi-Fi) and/or specific medical software integrator application programming interface (API) being used in a particular medical environment. Alternatively, the RF signal may connect to existing bed side gear by re-creating analog ECG signals for the RF packet that wire directly into the analog sensor inputs of existing gear. This last option allows wireless leads to be used with existing stationary bed-side monitors independent of data protocol, IT infrastructure and manufacturer of equipment.

As described herein, known sensor, transmitters and batteries may be packaged in hermetically sealed packages. A biometric lead set may include one or more such packages. In some embodiments, two or more such packages may be interconnected. In the embodiment illustrated herein, the interconnections are implemented with wires. Components may be distributed over multiple packages. For example, a battery may be sealed in one package, a transmitter in another and a power receiving device, for recharging the battery, may be in yet another package. One or more of the packages may contain a controller that generates control signals for the components in its package and/or components in other packages interconnected by the wires. However, it should be appreciated that it is not a requirement of the invention that there be a one-to-one relationship between components and packages. Some packages, for example, may contain two or more such components, while other packages may contain none. Such a distribution of components is possible in some embodiments because the packages may be interconnected by wires.

Accordingly, an improvement on ECG monitoring technology may use known measurement methods, meaning that the basic contact/non-contact passive lead technology and human interface being proposed are the same as existing solutions that have been reliably deployed for years. There are true RF non-contact solutions in the market that use millimeter wave technology to discern pulse movements on the human body. However, this approach falls short of producing a true ECG waveform required for a wide array of medical settings. Instead, some embodiments provide to the lead sets themselves a level of miniaturization and integration found, for example, in telecommunications applications. This is primarily accomplished by combining die-scale active integrated circuits (ICs) and passive components into multi-chip modules (MCMs).

Figure 5:
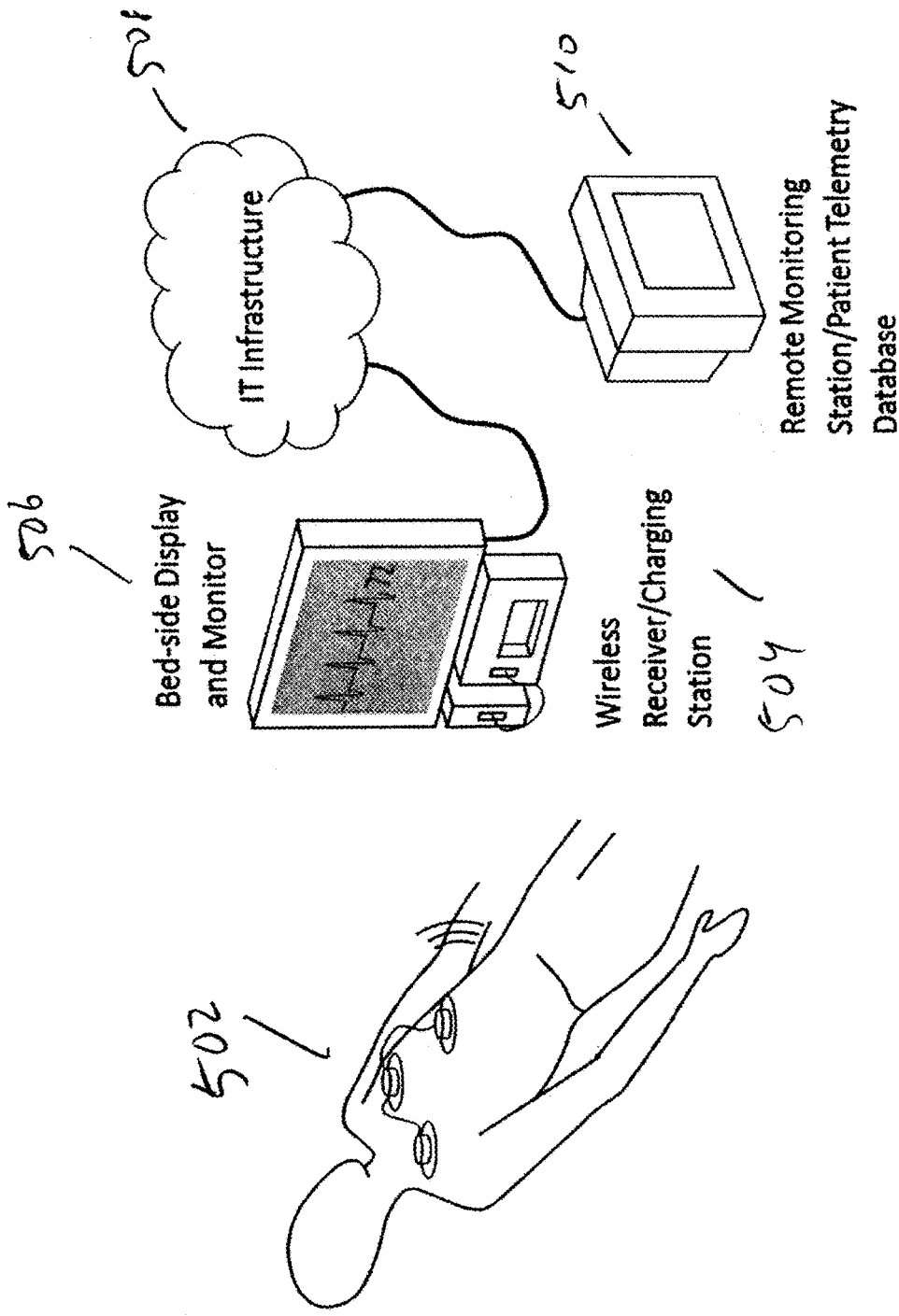
FIG. 5 is a schematic illustration of available components in a wireless ECG monitoring system in accordance with some embodiments.

FIG. 5 is a schematic illustration of available components in a wireless ECG monitoring system, in accordance with some embodiments. Wireless biometric lead set 502, which may include three (as shown) or more leads, is capable of transmitting monitored biometric data wirelessly, without the use of a separate portable unit for transmission, although a separate portable unit may be incorporated as a further package in a wireless lead set in some embodiments. Lead set 502 is attached to a patient's body using adhesives such as tape and/or electrically-conducting gels to ensure adequate electrical conductivity.

An interface device may be provided to interface data received wireless from a wireless lead set. In this example, the interface devices is wireless receiver/charging station 504, which is equipped to receive signals transmitted from wireless patient leads 502a-c, and additionally, in some embodiments, is enabled to provide charging functions for one or more wireless biometric lead sets. Wireless receiver/charging station 504 may also be equipped to provide digital information to bed-side monitor 506, and in some embodiments may interoperate with standard bed-side monitor systems. Additionally, IT infrastructure 508 and remote monitoring station/patient telemetry database 510 are provided, and bed-side display and monitor may allow these systems to access the received biometric data.

The use of a wireless biometric lead set (also abbreviated herein as "lead set") restructures the basic components of wireless leads into an integrated solution, where the electronics are fully contained and potentially distributed within the lead set itself. Significantly, the concept of a disposable or reusable lead set used in conjunction with an electronics base is modified to physically resemble and/or approximate the schematic illustrations shown in FIGS. 6A and 6B.

Figure 6B:
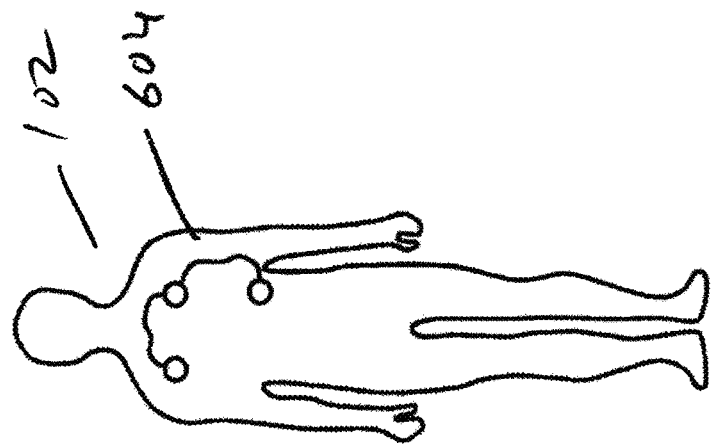
FIG. 6A and FIG. 6B are schematic illustrations of patients wearing a lead set in accordance with some embodiments.
Figure 6A:
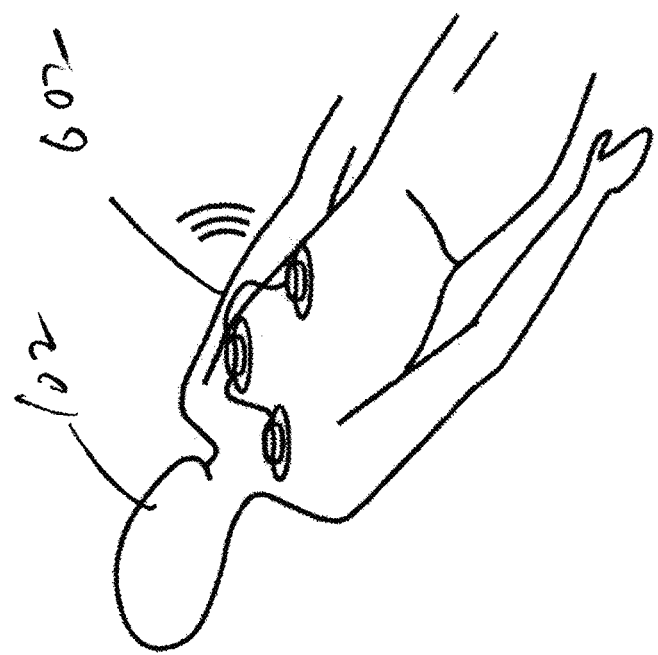

FIGS. 6A and 6B are schematic illustrations of patients wearing a lead set in accordance with some embodiments. FIG. 6A depicts a perspective view of a patient 102 wearing lead set 602, which is enabled to transmit data wirelessly without a portable unit by the integration of power source, wireless transceiver, and/or electronic components such as those described previously herein as being present in bedside monitor/portable unit 404. The integrated components have a low profile and sit on top of the electrode pads typically used for ECG sampling electrodes. FIG. 6B depicts an alternate view of patient 102 wearing lead set 604.

The power source, ICs and/or MCMs in this case may be hermetically sealed within plastics of the leads themselves, permitting an incrementally smaller form factor than existing solutions. Electronics can be distributed within the lead set, where each lead contains an analog contact/non-contact sensor to be applied to the patient. Each such sensor may be encapsulated to form a package, which may include an amplifier, battery, analog conversion electronics, processor, and/or the RF system/SoC. It is important to note that the miniaturization of the electronics can permit variations of distributions of the functional elements across and within the leads, including integrating all of the electronics into one "master" lead with any number of passive leads. In some embodiments, an energy harvesting/wireless recharging coil may be provided in conjunction with or in place of a battery, to provide power to the electronics within the sealed lead.

Figure 7:
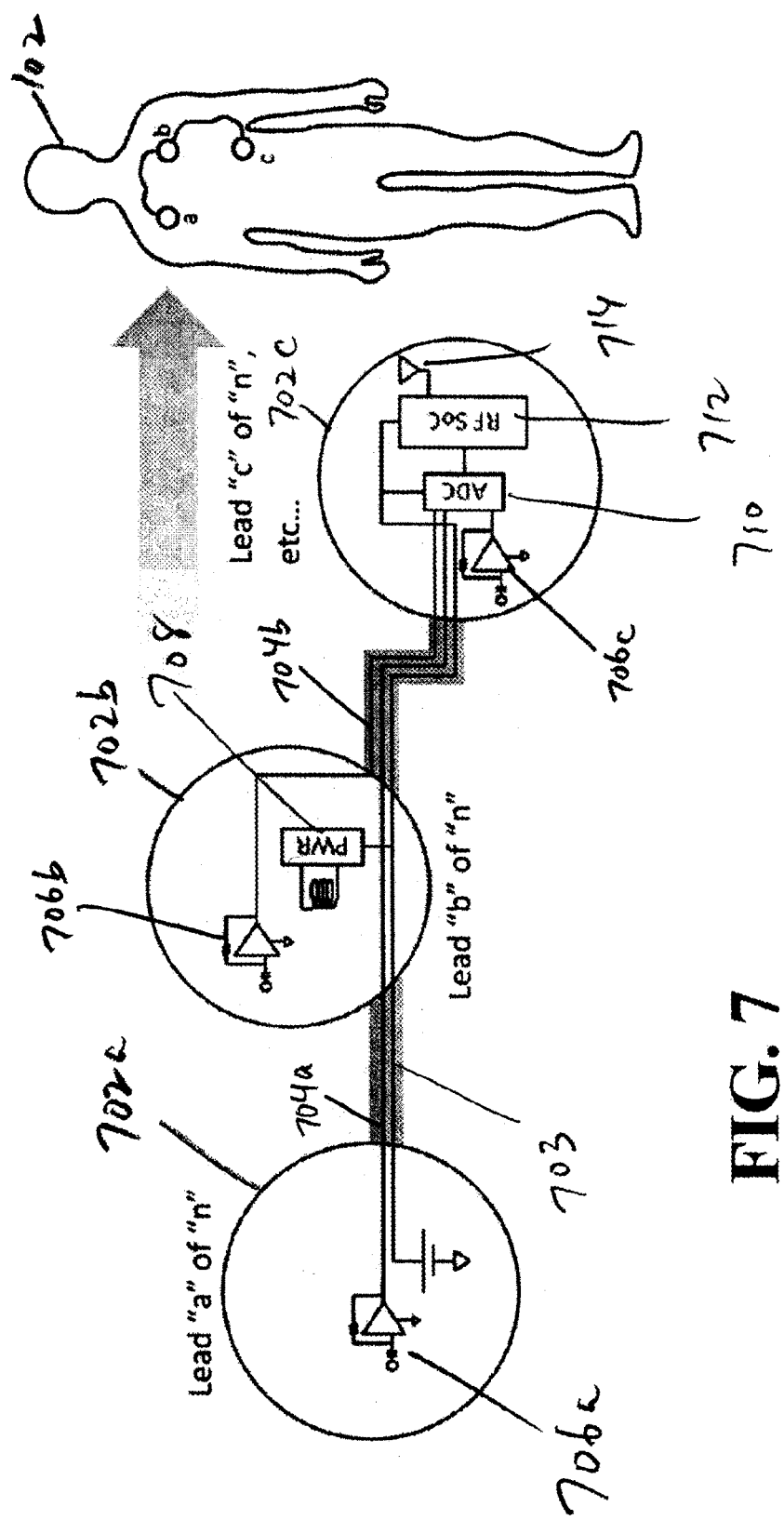
FIG. 7 is a schematic illustration, showing in more detail, components of system using a wireless lead set in accordance with some embodiments.

FIG. 7 is a schematic illustration, showing in more detail, components of system using a wireless lead set in accordance with some embodiments. Packages 702a, 702b, and 702c are shown. Package 702a is electrically interconnected to package 702b and also to package 702c, specifically, by power conductor 703 and a signal conductor 704a. Power conductor 703 is connected to all packages, e.g., package 702a, 702b, and 702c. Package 702b is also electrically interconnected to package 702a and 702c via signal connection 704b. Signal connection 704b does not connect to package 702a, as, in the embodiment illustrated, signals acquired by each of the packages is routed to package 702c. Package 702c is thus connected via three electrical conductors to the other packages 702a and 702b, such that an electrical power connection is shared by all package and an individual connector is provided from each lead to package 702c. The configuration shown is exemplary and other configurations may be used, in other embodiments, to route signals and power among the packages.

Each of packages 702a, 702b, 702c include respective biometric sensors. Each package may also include signal conditioning circuitry, which in FIG. 7 includes amplifiers 706a, 706b, 706c. These amplifiers may be used for picking up electrical impulses from patient 102, for example, picking up electrical signals for providing an ECG. Amplifiers 706a-c amplify the electrical connections provided by an electrode (not shown) on the surface of the hermetically sealed packages of each of packages 702a-c, which is in physical contact with the patient, thereby allowing monitoring of electrical impulses. Signal lines 704a, 704b deliver the electrical signals from each biometric sensor to lead 702c via their own conductors.

Package 702b, in addition to providing a biometric sensor, also provides power source 708, in some embodiments. As shown, power source 708 is an inductive coil coupled with a battery for wireless rechargeability and mobility. In some embodiments, the power source may be disposed in another package.

Package 702c, in addition to providing a biometric sensor, also provides ADC 710, RF SoC 712, and antenna 714. In other words, package 702c provides all necessary functions to serve as a wireless transceiver. All biometric signals are received at package 702c via electrical conductors 704a, 704b, digitized, and then transmitted to a wireless receiver, such as wireless receiver 504. Other configurations of a wireless transceiver may also be used, in some embodiments. SoC 712 may also include a memory, in some embodiments, for storing digital values output by ADC 710 which correspond to signals that have been received from the biometric sensors on any of packages 702a-c. The use of a SoC that includes many components may allow package 702c to be comparable in size to the other packages.

As described above, the various components enabling functions of a wireless biometric lead set are thereby distributed among packages 702a-c. In some embodiments, the various components may be disposed in alternate configurations or in a different order. In some embodiments, more than three packages may be provided. In the case where n packages are provided, in one embodiment, the power source is disposed at the n−1th lead, while the wireless transceiver is disposed at the nth lead.

Theory of Operation

In the paragraphs which follow, principles, techniques, apparatuses and methods are disclosed that relate to the operation of various embodiments.

Hermetic Sealing

The presence of hatches and connectors in these products present challenges with waterproofing and general compliance with cleaning/sterility modalities. To paraphrase, electrical connectors and user-accessible battery hatches are difficult to waterproof and can be aggregation points for moisture and otherwise contamination. By hermetically sealing all of the electronics, power source, and a contactless charging method into the leads themselves, the leads can be immersed indefinitely without concern for intrusion of foreign matter. Hermetically sealed packages thus offer advantages in a health care environment such as a hospital, as they permit a set of leads to be sanitized (UV sterilized, chemically washed or autoclaved in a low-temperature autoclave at below 85 degrees C.) and then re-used.

Low Power Operation

The miniaturization of existing technologies does not come without deployment issues that are addressed in some embodiments disclosed herein. For the most part, the analog sensing of ECG data does not require significant amounts of power given silicon process improvements over recent years: Small modern microcontrollers capable of collecting ECG data can run indefinitely powered only from minor kinetic, capacitive, or inductive coupling/harvesting mechanisms. However, the handling of RF data for appreciable time spans and useful broadcasting ranges requires a comparatively more significant power source, such as a rechargeable battery.

RF power levels and product operational life between charges becomes a significant issue when considering the overall form factor of the industrial design vis-à-vis the battery requirements. Accordingly, rechargeable batteries in existing wireless ECG units require replacement (requiring access hatches in the product) or wired charging connectors.

A key to miniaturizing the battery and therefore form factor without compromising functionality is to ensure that low power and power-saving electronics design techniques are applied to ECG and other patient vital sign monitoring. In some embodiments, use of the lowest possible power RF transmission scheme such as low power Bluetooth or proprietary RF (similar to existing solutions) is used to enhance power saving characteristics in a duty-cycled method. Although not precluded, Wi-Fi generally requires much more continuous (i.e., high duty cycle) processing and wider RF spectrum usage and is therefore not necessarily conducive to low power operation of electronics in some embodiments.

In some embodiments, a processor may be used in sleep/low power mode to significantly cut down on power consumption, and then may be woken to perform functions at different intervals. These intervals may be periodic. The first interval may define more-frequent data collection and the second interval may be less-frequent data transmission of multiple samples aggregated since a prior transmission. The first interval is shorter than the second interval, and the second interval may be a multiple of the first interval, in some embodiments. As data is accumulated during the first interval of the duty cycle but not transmitted, the untransmitted data may be retained in a memory for subsequent transmission.

Figure 8:
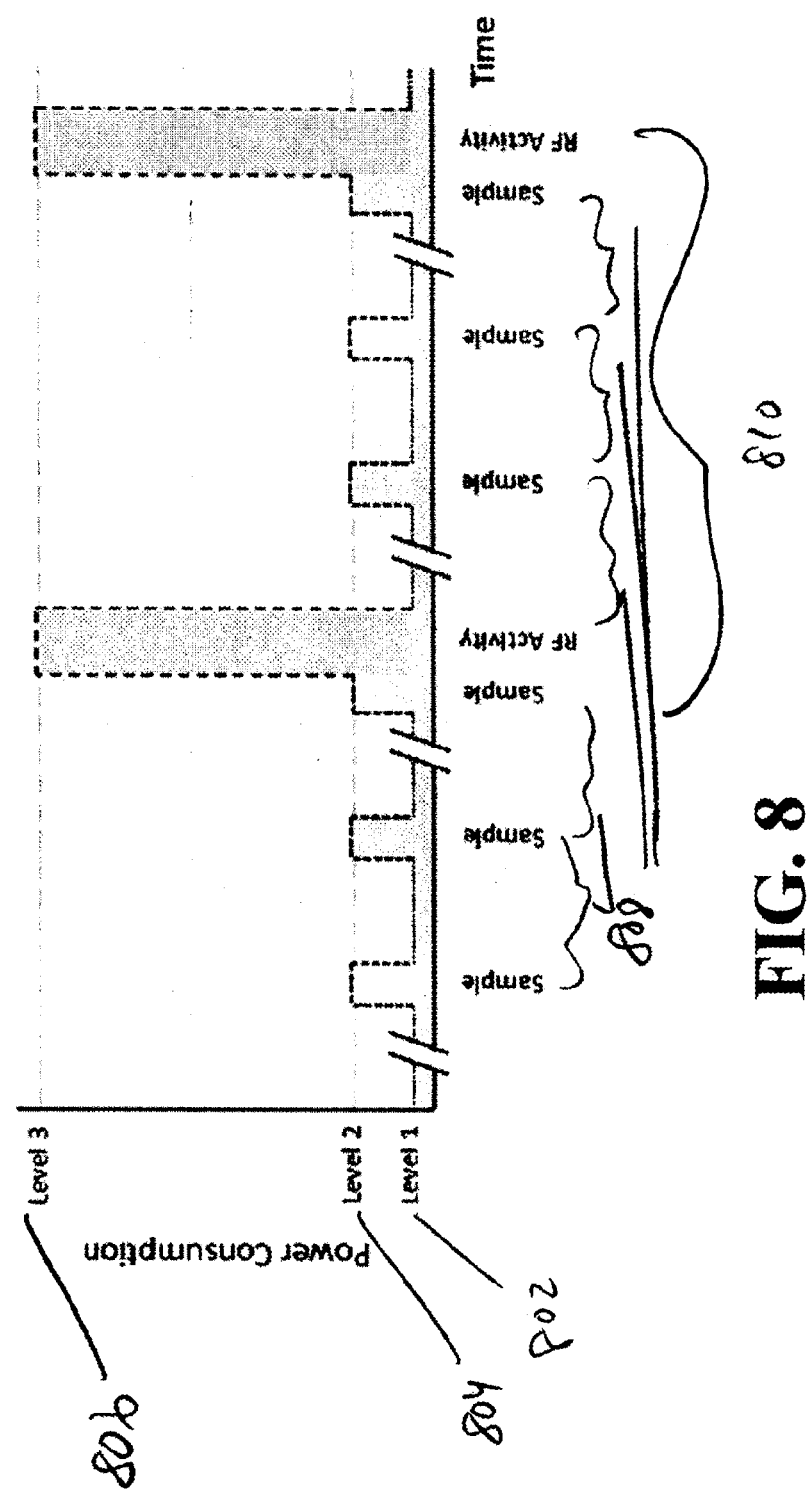
FIG. 8 is a timing diagram showing operation of a wireless lead set in multiple power saving modes in accordance with some embodiments.

FIG. 8 is a timing diagram showing operation of a wireless lead set in multiple power saving modes in accordance with some embodiments. A base level of power consumption 802 (Level 1) is identified, as is an elevated level of power consumption 804 (Level 2) and a high level of power consumption 806 (Level 3). Sampling is shown to occur at intervals 808, while RF activity is shown to occur at intervals 810. Timing generation for the intervals shown may be performed by a clock inside of a processor, or by the RF SoC, in some embodiments.

While the number of levels and relative periods and frequencies thereof can be modified, the base level (Level 1) may correspond to a scenario in which various components, such as a processor, RF SoC, and/or its peripherals are in sleep mode, i.e. in a non-functional state, conserving the most power (drawing very low quiescent current). Level 2 power consumption occurs when the sensor electronics wake and perform analog measurements, ECG or other vital patient data. The processor can either store the sample and resume sleep mode or continue to an even higher level of current draw, Level 3 power consumption, where patient data is ultimately transmitted, based on the timing of intervals 808 and 810.

In some embodiments, when charging, the lead set detects the presence of charging current and ceases collection and transmission of data. This is useful to minimize battery charging time when the leads are removed from the patient.

Recharging the Leads

In some embodiments, a small battery is embedded into the plastics of the packages, which has the effect of eliminating a connector or hatch. Thus, the battery is charged with the assistance of an embedded inductive pickup coil also embedded in the lead set, a concept not leveraged by existing wireless ECG units that typically deploy "baggies" or other disposable means of protecting the electronics equipment from contamination while in use. In the case of ancillary disposable barrier usage, the patient contact leads are often disposable as well to reduce risk of migration of infection from one patient to another. The use of inductive coils and batteries is designed to reduce the amount of disposables used while ensuring a compliant, cleanable platform by sealing the battery and charging/harvesting electronics in a connector-less format. The leads, when not in use, are placed on recharging platforms, such as a holder at the base station, or in an electronics enclosure equipped with e.g., inductive or magnetic power coils tuned to match the coil embedded in the leads.

In some embodiments, recharge status may be shown on the front of a lead, or on the base station, or on the holder, or on another user-visible location.

Initial Deployment and Association of Lead Data

With RF data, transmitted data packets may be in range of multiple receivers, where only one or a specific subset of receivers may be the intended recipient of the data. Other wireless technologies typically require the presence of a hardware "token" to ensure that data sent from one unit is only decoded by one other with a manual actuation event (switch or button press). In some embodiments of the present disclosure, a proximity "key" similar to those used in keyless (card) access systems may instead be used in each lead set to differentiate its RF data stream from any other. The key may be communicated wirelessly to the base station at the time of association (i.e., upon request for association). The key may be transmitted wirelessly at a very low power, thereby reducing the likelihood that the wrong receiver may receive the key during association. The key may be encoded in the lead set and sent to the base station. However, the key may alternatively be communicated to the lead set from the base station.

A limitation to the hardware token or dongle concept is that RF data can usually only be received at one location. Proximity-based data encryption allows a commensurate level of security while not restricting the number of receivers capable of simultaneously and securely handling incoming lead data. Additionally, the usage of proximity technology allows synchronization and association of data in an RF frequency band other than the band being used for communication by the leads and receivers. Following is a block diagram of the lead synchronization process.

In some embodiments, bar codes may be used in place of, or supplemental to, wireless communication of digital keys for association.

In the case described below where an integrated charger and base station are present with the bed-side monitor and equipment, the act of removing the lead set from the charger/base station (detection of a stop-charging event) may automatically trigger a proximity sense and/or RF association event. Such a trigger, for example, may cause one device to begin transmitting, possible for a limited period of time, the key and the other to begin scanning for such a transmission. In some embodiments, removal from a base station or a charging location also may be used as a trigger to cause the leads to either automatically begin collection and RF transmission of data or wait for a proximity scan to begin data transmission.

Figure 9:
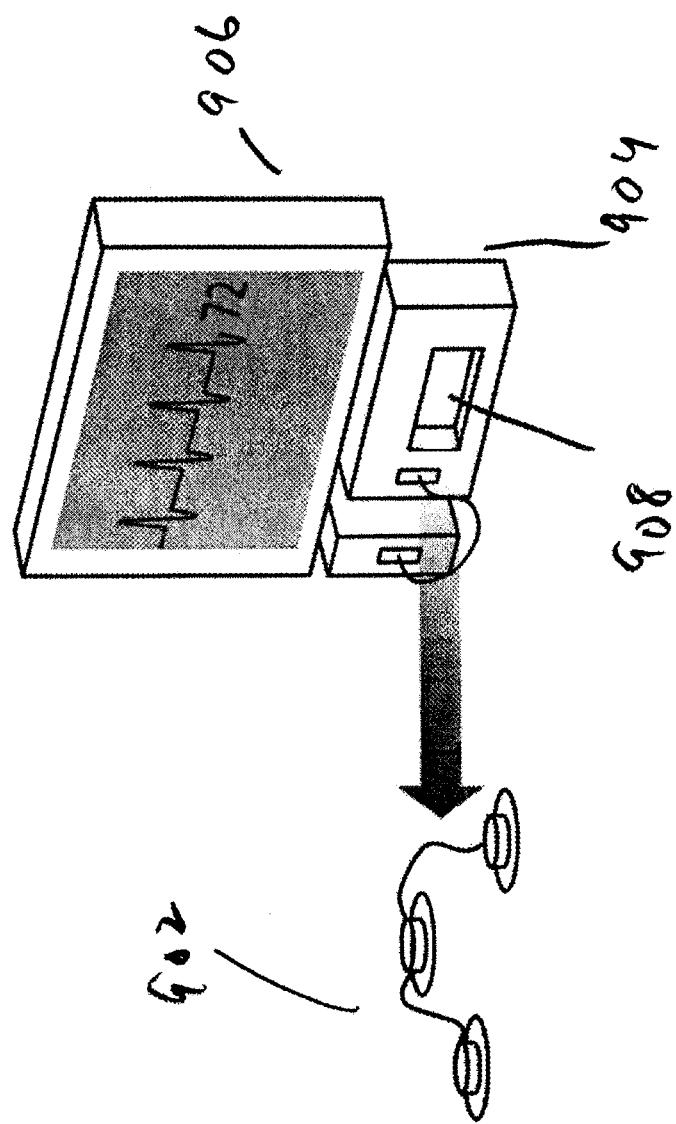
FIG. 9 is a sketch of removal of leads and automatic RF association of a wireless lead set to a monitoring device.

FIG. 9 is a sketch of removal of leads and automatic RF association of a wireless lead to a monitoring device. Lead set 902 is depicted as being removed after charging from holder 908, which is part of charger/base station 904. In the illustrated embodiment, holder 908 is a cavity containing a wireless or wired charging modality, such as, for instance, an inductive charging coil configured to couple with an inductive charging coil in one of the hermetically sealed packages. Charger/base station 904 is coupled with bed-side monitor and equipment 906. In some embodiments, removal during charging may be supported and may act as a trigger.

The location of a lead set may change when the lead set is already in use but the patient is being transferred from one location to another. To ensure continuity of patient monitoring, data maybe collected and maintained in a temporary rolling buffer in the lead itself. However, at some point, the lead data is re-associated to a new location with the proximity sensor and a third piece of equipment. In some embodiments, a handheld proximity sensor/wireless receiver may be used to make the association when the lead set is separated from a base station with which it is to be associated by a distance greater than a range of short range communication used for making an RF association.

Figure 10:
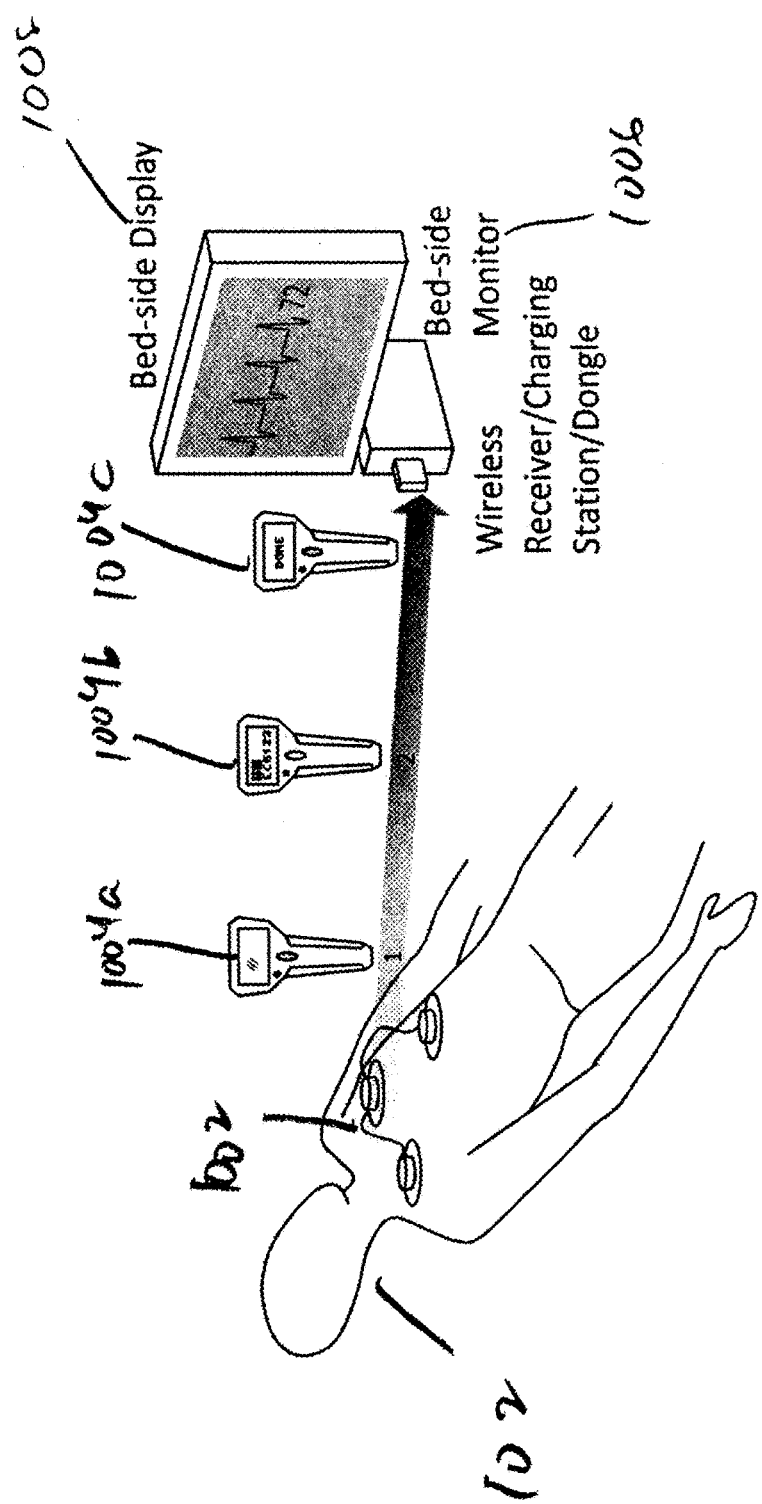
FIG. 10 is a sketch of a partially manual approach for RF association of a wireless lead set to a monitoring device using a proxy device.

FIG. 10 is a sketch of a partially manual approach for RF association of a wireless lead set to a monitoring device using a proxy device. Depicted are patient 102; wireless lead set 1002; handheld proximity sensor 1004 at various stages (1004a, 1004b, 1004c); bed-side monitor 1006; and bed-side display 1008. The depicted screens of the handheld proximity sensor 1004 relate to the steps described below.

The handheld proximity sensor 1004 is used to "transfer" the association of the data coming from the leads to base station, or in the case of FIG. 10, the wireless receiver of a monitoring device or "dongle" (which may be used if a local charging station is not required at the particular bed-side monitor) that plugs directly into the bed side monitor. First, handheld sensor at stage 1004a is positioned to within a few inches of the leads, and the "Associate" button is pressed with the users thumb. If detection is successful, the handheld sensor will detect and store the proximity key within the lead set and display the code on its screen. The handheld sensor may be moved to position 1004b, including the code. While the data is "captured" on the screen of the handheld sensor, the handheld sensor is carried to the receiving station (or in this case, bed-side monitor with a receiver dongle) at stage 1004c. In the final step, pressing the "Associate" button on the handheld sensor causes it to communicate the lead proximity code to the receiver, where the receiver can then begin to decode and display the wireless data from the associated lead set. The leads will continue to broadcast the data until battery power is exhausted, at which point the leads may be cleaned, recharged, and redeployed.

Wide Area Operation

Figure 11:
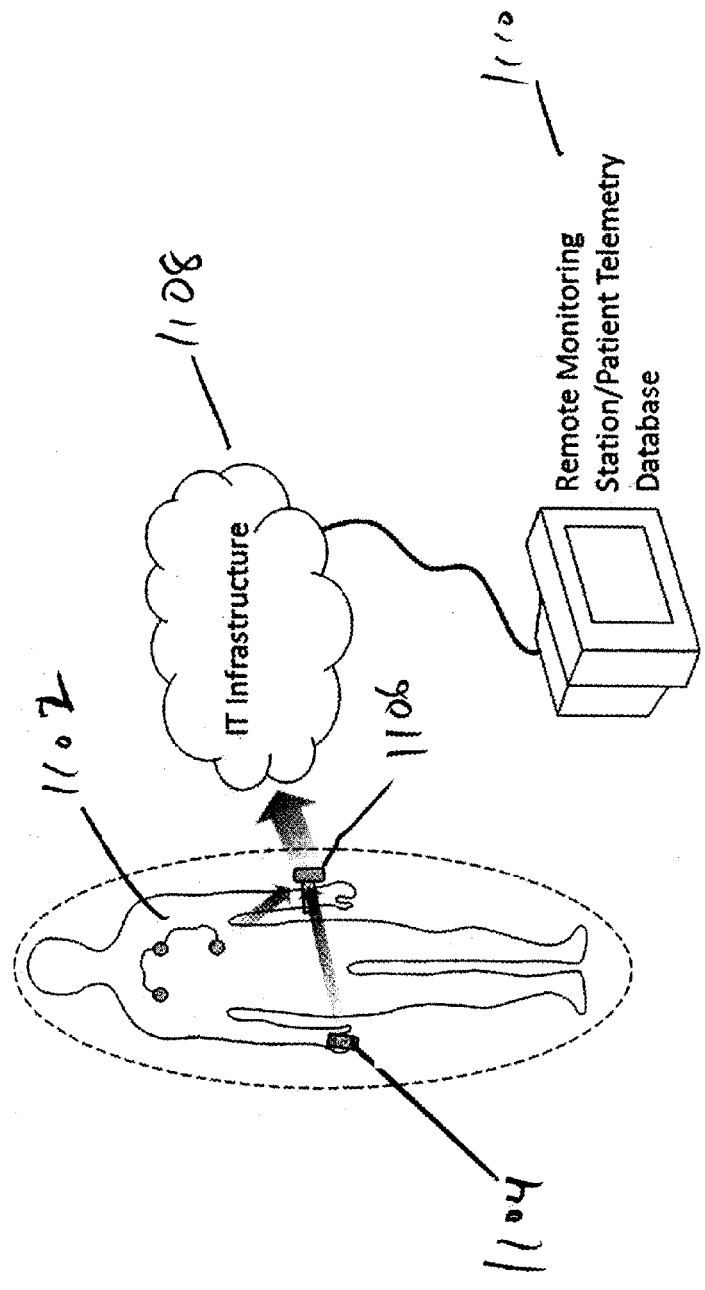
FIG. 11 is a sketch of an embodiment in which a wireless lead set interfaces with IT infrastructure of a health care facility.

FIG. 11 is a sketch of an embodiment in which a wireless lead set interfaces with IT infrastructure of a health care facility. Wireless lead set 1102 is shown, as is fingertip pulse oximeter 1104, both of which are communicating wirelessly with portable unit 1106. Portable unit 1106 communicates wirelessly, via wireless infrastructure such as Wi-Fi access points (not shown), with IT infrastructure 1108 without the intermediation of a bed-side display. This communication may be enabled by the portable unit 1106, IT infrastructure 1108, or by various combinations of both. IT infrastructure 1108 may be in communication with remote monitoring station/patient telemetry database 1110.

Typically, the sensors described herein, whether ECG, temperature, pulse oximeter, etc., for the purposes of security and battery saving, may have a range of about 25-30 feet. However, in many cases, to improve mobility, further range may be desired. In this case, and as depicted in FIG. 11, a mobile "medical area network" is defined, which may be a localized region where localized patient data is aggregated and then re-broadcast via another medium such as Wi-Fi where wireless data can be forwarded to or received directly by desired institution infrastructure. The Network of Medical Area Devices (NoMAD) allows mobility even beyond the range of the sensors (leads) themselves by deploying a protocol/medium translating device, also worn by the patient.

A monitoring system as described herein may be implemented with any of numerous general purpose or special purpose computing system environments or configurations. The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An interface device adapted to configure a monitoring device for operation with a wireless biometric lead set, the device comprising:
a charging station for the wireless biometric lead set;
a connector configured to connect to a monitoring device;
a wireless receiver; and
a controller, adapted to perform a radio frequency (RF) association with the wireless biometric lead set and to transfer data received from the associated wireless biometric lead set from the receiver through the connector;
wherein the controller is configured to perform an RF association routine based on an indication that the wireless biometric lead set is disconnected from the charging station.

2. The interface device of claim 1, further comprising:
a holder for holding the wireless biometric lead set at the charging station.

3. The interface device of claim 1, wherein the interface device comprises a dongle configured for insertion into a lead port of the monitoring device;
wherein the dongle comprises a wireless receiver.

4. The interface device of claim 1, wherein the wireless biometric lead set comprises:
a plurality of hermetically sealed packages, each of the plurality of hermetically sealed packages containing a biometric sensor and one or more electronic devices, each of the plurality of hermetically sealed packages being individually hermetically sealed, and each of the plurality of hermetically sealed packages being configured to be attached to a body;
a plurality of conductors interconnecting the plurality of hermetically sealed packages;
a power source; and
a transceiver.

5. The interface device of claim 4,
wherein the one or more electronic devices comprise circuitry for conditioning a signal from a biometric sensor.

6. The interface device of claim 4, wherein:
the power source comprises at least one of a battery and an energy harvesting and storage module.

7. The interface device of claim 6, wherein:
the plurality of hermetically sealed packages comprises a first hermetically sealed package, a second hermetically sealed package, and a third hermetically sealed package; and
the power source is disposed within the first hermetically sealed package, and
the transceiver is disposed within the second hermetically sealed package.

8. The interface device of claim 7, further comprising:
a wireless recharging coil disposed within the third hermetically sealed package.

9. The interface device of claim 5, wherein the biometric sensor contained within each of the plurality of hermetically sealed packages is an electrocardiograph (ECG) sensor.

10. The interface device of claim 4, wherein the wireless biometric lead set further comprises:
a memory,
wherein the controller is configured to:
accumulate in the memory a plurality of samples from a biometric sensor in a hermetically sealed package of the plurality of hermetically sealed packages, the plurality of samples being accumulated at first intervals; and
transmit, at second intervals longer than the first intervals, the plurality of samples accumulated in the memory.

11. A method of operating a wireless biometric lead set for monitoring a patient, the method comprising:
receiving, via wireless communication, a key associated with the wireless biometric lead set;
associating the key with a monitoring station;
measuring biometric data with the wireless biometric lead set;
transmitting the measured biometric data from the wireless biometric lead set in connection with the key;
at the monitoring station, selecting data for patient monitoring based on the associated key;
wherein the measuring of the biometric data with the wireless biometric lead set is performed in response to an indication that the wireless biometric lead set is removed from a charging station.

12. The method of claim 11, wherein:
the wireless biometric lead set is connected to the monitoring station for charging and disconnected from the monitoring station for use in monitoring a patient.

13. The method of claim 11,
wherein receiving the key associated with the wireless biometric lead set comprises:
with a proxy device in proximity to the wireless biometric lead set, wirelessly receiving the key;
moving the proxy device in proximity to the monitoring station; and
with the proxy device in proximity to the monitoring station, transferring the key to the monitoring station.

14. The method of claim 11, further comprising:
accumulating measured biometric data samples within the wireless biometric lead set;
transmitting, at intervals, the accumulated measured biometric data samples.

15. The method of claim 14, wherein:
the wireless biometric lead set operates in a first power consumption mode when the accumulated measured biometric data samples are transmitted and operates at a second power consumption mode during intervals in which the accumulated measured biometric data samples are not transmitted, more power being consumed in the first power consumption mode than in the second power consumption mode.

16. The method of claim 15, wherein:
the intervals are first intervals;
the measured biometric data samples are collected at second intervals, shorter than the first intervals; and
the second power consumption mode comprises a first submode during which the measured biometric data samples are being acquired and a second submode during which the measured biometric data samples are not being acquired.

17. The method of claim 16, wherein:
the measured biometric data samples comprise samples from a plurality of ECG sensors.

18. The method of claim 17, wherein:
selecting data for patient monitoring comprises monitoring a first patient; and
the method further comprises:
sterilizing the wireless biometric lead set and reusing the wireless biometric lead set for monitoring a second patient.

19. The method of claim 13, further comprising:
accumulating measured biometric data samples within the biometric lead set;

transmitting, at intervals, the accumulated measured biometric data samples.

20. The method of claim 19, wherein:
the wireless biometric lead set operates in a first power consumption mode when the accumulated measured biometric data samples are transmitted and operates at a second power consumption mode during intervals in which the accumulated measured biometric data samples are not transmitted, more power being consumed in the first power consumption mode than in the second power consumption mode.

21. The method of claim 13, wherein receiving the key associated with the wireless biometric lead set is performed when a patient wearing the biometric lead set has been relocated by a distance greater than a communication range associated with the wireless biometric lead set.

* * * * *